(12) United States Patent
Linares et al.

(10) Patent No.: US 8,900,318 B2
(45) Date of Patent: *Dec. 2, 2014

(54) IMPLANTABLE HALLUX JOINT ASSEMBLY WITH SPHERICAL INTER-SUPPORT

(71) Applicants: Miguel A. Linares, Bloomfield Hills, MI (US); Linares Medical Devices, LLC, Auburn Hills, MI (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 216 days.

This patent is subject to a terminal disclaimer.

(21) Appl. No.: 13/630,052

(22) Filed: Sep. 28, 2012

(65) Prior Publication Data

US 2013/0090740 A1 Apr. 11, 2013

Related U.S. Application Data

(60) Provisional application No. 61/540,171, filed on Sep. 28, 2011.

(51) Int. Cl.
*A61F 2/42* (2006.01)
*A61F 2/30* (2006.01)

(52) U.S. Cl.
CPC ..... *A61F 2/4225* (2013.01); *A61F 2002/30014* (2013.01); *A61F 2002/30224* (2013.01); *A61F 2002/30253* (2013.01); *A61F 2002/30563* (2013.01); *A61F 2002/3064* (2013.01); *A61F 2002/30642* (2013.01); *A61F 2002/30878* (2013.01); *A61F 2002/30971* (2013.01); *A61F 2002/4235* (2013.01)
USPC ..................... 623/21.19; 623/21.15

(58) Field of Classification Search
CPC ....... A61F 2/42; A61F 2/4225; A61F 2/4241; A61F 2/4261; A61F 2002/4243; A61F 2002/4246; A61F 2002/4248
USPC .......... 623/17.14, 19.11, 19.12, 20.11, 20.12, 623/20.13, 20.21, 20.22, 20.23, 21.13, 623/21.15, 21.16, 21.17, 21.18, 23.4
See application file for complete search history.

(56) References Cited

U.S. PATENT DOCUMENTS 3,992,726 A * 11/1976 Freeman et al. ............. 623/23.4
5,458,648 A    10/1995 Berman et al.
6,716,249 B2   4/2004 Hyde
(Continued)

FOREIGN PATENT DOCUMENTS

DE        10358307 A1   6/2006
WO   WO-2006099886 A1   9/2006

*Primary Examiner* — David Isabella
*Assistant Examiner* — Rokhaya Diop
(74) *Attorney, Agent, or Firm* — Gifford, Krass, Sprinkle, Anderson & Citkowski, P.C.; Douglas J. McEvoy

(57) ABSTRACT

A multi-component hallux joint assembly incorporated into reconditioned end surfaces established between an upper metatarsal bone and an opposing lower proximal phalanx bone. A first component is anchored into a reconditioned end surface of the metatarsal bone and exhibits a first exposed support surface. A second component is likewise anchored into a reconditioned end surface of the proximal phalanx and exhibits a second exposed support surface. A spherical shaped intermediate component is supported in at least one of eccentric or rotational fashion between the first and second anchored components.

11 Claims, 4 Drawing Sheets

(56) References Cited

U.S. PATENT DOCUMENTS 7,461,978 B2 * 12/2008 Pope et al. .................... 384/492
2002/0111690 A1 8/2002 Hyde
2012/0209337 A1 8/2012 Weinstein

* cited by examiner

IMPLANTABLE HALLUX JOINT ASSEMBLY WITH SPHERICAL INTER-SUPPORT

CROSS REFERENCE TO RELATED APPLICATIONS

The present application claims the priority of U.S. Ser. No. 61/540,171 filed Sep. 28, 2011.

FIELD OF THE INVENTION

The present invention discloses an artificial joint assembly, such as is particularly configured for employing as a retrofit hallux (big toe) joint, and which combines multiple artificial components incorporated into first and second reconditioned joint defining surfaces for providing increased wear life in tandem with evenly distributed wear pattern/profile as well as enhanced flexibility and mobility.

BACKGROUND OF THE RELEVANT ART

The prior art is documented with examples of toe joint assemblies, such as associated with the big toe or hallux joint. These include the great toe joint implant and method of implantation depicted in U.S. Pat. No. 5,458,648, to Berman et al., in which a nonconstrained total great joint implant for the metatarsophalangeal joint includes a first component with a convex, partially spherical surfaced ending in a rear surface from which a longitudinally asymmetric implantation stem projects having a flange on the dorsal side of the implant which extends the convex surface past the rear surface.

Additional examples include the modular joint prosthetic and method of implantation set forth in Hyde, U.S. Pat. No. 6,716,249, which is applicable to either a finger or toe joint assembly. Weinstein, US 2012/0209337 discloses a method and apparatus for preparing fusion of such as finger and toe joints and which includes one or more of complementary ball and socket joint reamers.

SUMMARY OF THE PRESENT INVENTION

The present invention teaches a multi-component hallux joint assembly which is incorporated into reconditioned end surfaces established between an upper metatarsal bone and an opposing lower proximal phalanx bone. A first component is anchored into a reconditioned end surface of the metatarsal bone and exhibits a first exposed support surface. A second component is likewise anchored into a reconditioned end surface of the proximal phalanx and exhibits a second exposed support surface.

An intermediate component is supported in at least one of eccentric or rotational fashion between the first and second anchored components. The intermediate component can include a spherical shaped component.

Other features include each of the anchored components further exhibiting a concave surface for supporting the intermediate component. Each of the first, second and intermediate components may also be constructed of at least one of a metal, plastic, polymer or composite material.

The spherical shaped component can also be constructed of a multi-layer composition including a softer outer layer and at least one harder interior layer. First and second inner layers of the spherical component can also be configured for establishing an eccentric rotational interface therebetween.

In a further application, a plurality of surface projecting bearings can be mounted within an innermost spherical shaped portion of the spherical component, this facilitating the eccentric rotational interface. In a further variant, a grid pattern of lubricating grooves is defined in a surface of an innermost spherical shaped portion of the spherical component, this facilitating the eccentric rotational interface.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be disclosed with succeeding reference to the several depicted embodiments, the present invention discloses an artificial joint assembly, such as is particularly configured for employing as a retrofit hallux (big toe) joint, and which combines multiple artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's hallux joint existing between lower facing end of the metatarsal bone 1 and corresponding upper end of the proximal phalanx bone 2. Although not depicted in complete detail, the skeleton of the big toe consists of the first metatarsal bone (again at 1) which articulates with the proximal phalanx (again at 2) at what is defined as the primary metatarsophalangeal joint. The proximal phalanx also articulates with a distal phalanx (not shown) at a secondary distal joint.

It is further understood that certain applications could in theory include other joint applications, either human or other mammalian.

For purposes of ease and clarify of illustration, the various embodiments depicted further do not include reference to additional necessary components of the big toe joint, such as including associated muscles, tendons and ligaments, the inclusion of which are assumed and which collectively define a functioning and articulating wrist. Most basically, the big toe joint includes a plantar and two collateral ligaments which provide its range of articulating movement including each of flexion, extension, abduction and adduction.

Figure 1:
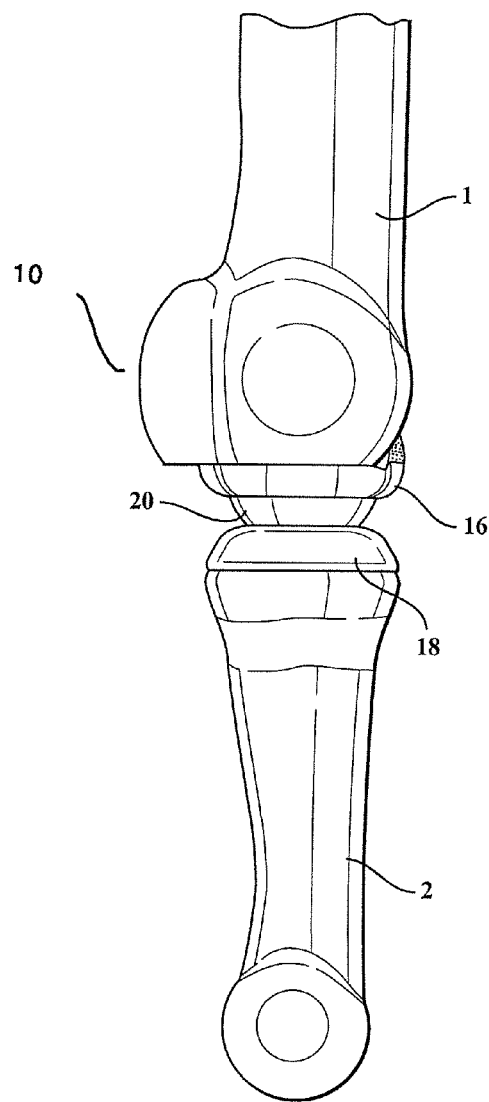
FIG. 1 is a first perspective view of a hallux implant assembly according to the invention.

Referring now to FIG. 1, a perspective view is generally shown at 10 of a toe implant assembly according to one non-limiting embodiment the invention and which is incorporated between an upper positioned metatarsal bone 1 and lower opposing proximal phalanx bone 2. These bones again collectively defining the metatarsophalangeal joint.

Figure 3:
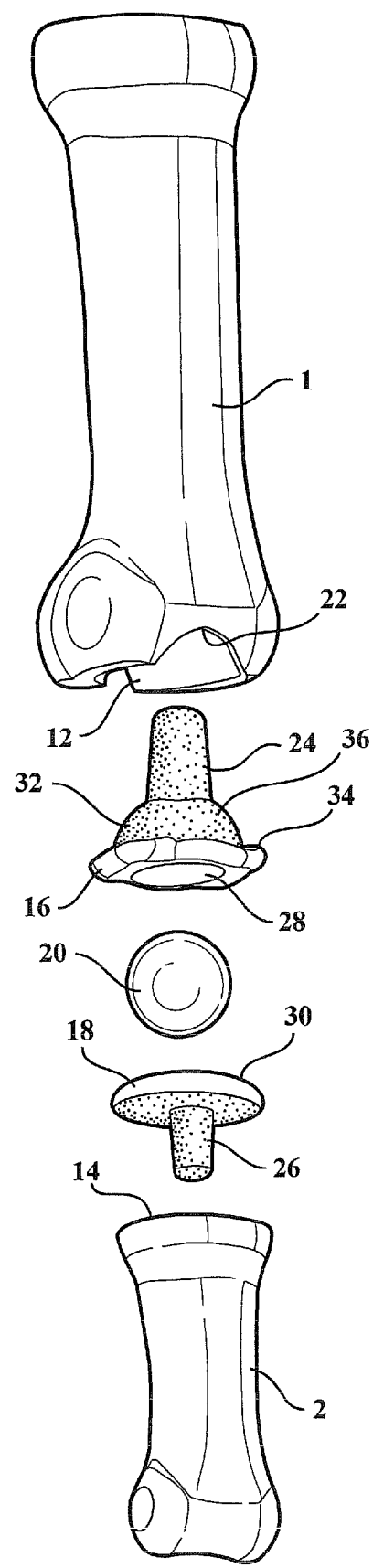
FIG. 3 is an exploded view of the hallux implant assembly of FIG. 1 and better illustrating the reconditioned end-configurations established between the associated metatarsal bone and proximal phalanx bone, combined with end face seating and marrow growth promoting implant support inserts with deep anchorage features in combination with intermediate positioned and eccentrically supported spherical portion.

Having described in some detail the bone construction of the hallux and as best illustrated in FIG. 3, each of the metatarsal 1 and proximal phalanx 2 bones are shown in exploded fashion with in situ reconditioning of the bone ends, this illustrated by first reconditioned/recessed end profile 12 configured into the bottom most end surface of the metatarsal 1, as well as opposing upper end facing and recessed/reconditioned profile 14 defined in the upper most opposing facing ends of the proximal phalanx 2. According to one non-limiting surgical procedure, such in situ reconditioning can occur following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain (avoid) or repair, where possible, natural ligament, cartilage and muscle associated with a normal functioning joint.

Although not shown, such reconditioning can be employed with minimal interference to such necessary additional elements of the big toe joint including associated ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial fashion concurrent with any necessary degree of refashioning or removal of damaged bone or joint.

A set of bone end installable implant portions are depicted at 16 and 18 with each exhibiting a rear facing profile suitable for anchoring into the respective reconditioned end face configurations 12 and 14 defined in the metatarsal 1 and proximal phalanx 2, respectively. Each of the implant portions 16 and 18 are constructed of any arrangement of metal, polymer, plastic, composite or other suitable material, with it further being understood that the individual pairs of components can be arrayed with any pattern of alternating materials, such that the components 16 and 18 being constructed of a first material, with an intermediate and inter-positioned spherical shaped bearing or ball portion 20 positioned therebetween and being constructed of a second alternating material.

Although depicted as a spherical shaped element, the present invention contemplates the thumb joint including any potentially reconfigurable opposing recessed profiles associated with implant portions 16 and 18, and which may further be provided in combination with an alternately (i.e. non-spherical) shaped intermediate component including any type of cylindrical, pseudo cylindrical, oblong, oval ellipsoidal or other smooth shape. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

A suitable medical adhesive, cement or other fastener can be employed for securing each of the upper implant component 16 into the respective reconditioned joint defining end surfaces 12 of the metatarsal 1, along with the lower implant component 18 being likewise secured into the reconditioned joint defining surface 14 of the proximal phalanx 2. As further best shown in FIG. 3, each of the reconditioned bone ends includes an interior extending aperture (best shown in shallow perspective by central aperture 22 referenced in FIG. 3 and associated with recess end profile 12 of the metatarsal bone 1, with corresponding end communicating aperture associated with the proximal phalanx 2 being largely hidden due to the angle in which it is presented). Each of the centrally located end apertures associated with the end face reconfigurations 12 and 14 are formed by a suitable bone drill in order to seat integrally formed and rearward extending anchoring stems, including that depicted at 24 associated with a rear mounting profile of the upper insert 16 into the lower end of the metatarsal 1 as well as also shown at 26 associated with rear mounting profile of the lower insert 18 and anchored into the mating interiorly recessed profile and associated drill aperture of the proximal phalanx 2.

Figure 2:
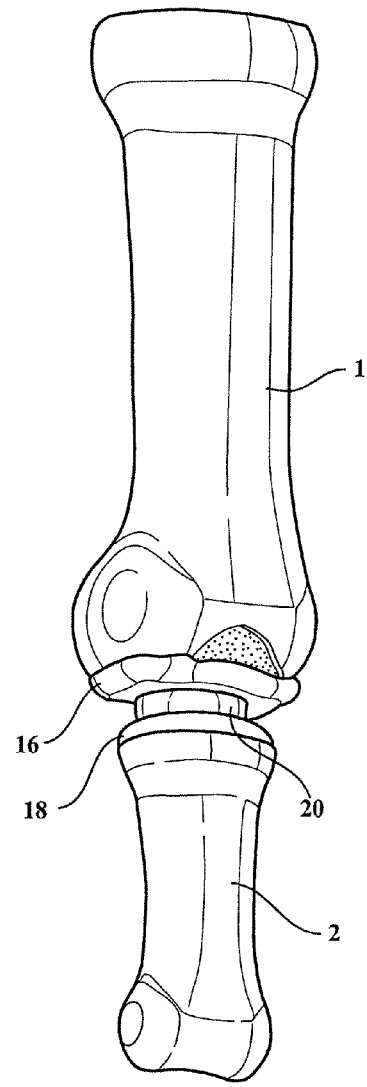
FIG. 2 is a second rotated view of the hallux implant assembly of FIG. 1.

Each of the end face mounted implants 16 and 18 further exhibits a concave exterior facing profile and which includes a more pronounced and substantially hemi-spherical concavity 28 (see also FIGS. 1 and 2) defined in the upper anchor 16, with an opposing and lesser pronounced/shallower concave seating cavity 30 associated with the lower insert 18. Upon securing the implants 16 and 18 within the reconditioned end face locations 12 and 14, these collectively define upper and lower seating locations for supporting the interposed spherical element 20 as again best depicted in the perspectives of FIGS. 1 and 2 and in a designed range of eccentric articulating ranges as permitted by the joint construction. As further previously noted, the concave shaped recess profiles can each be constructed of a smooth lubricant entrained or other polished plastic, composite or metal surface, with the exterior configuration of the spherical support 20 again being constructed of a material such as which reduces and equalizes wear profiles, as well as enhancing operational range and effectiveness.

As again previously indicated, additional configurations of muscles, ligaments, tendons are provided and can include both natural and/or synthetic materials which can be implanted or reconstructed in order to provide a dynamic and long-term implantable assembly. As shown in FIG. 3, the seating or inserting rear faces of the upper mounted implant portion 16 (including rear base convex surface 32 side of upper implant 16 defining an outer lip edge 34 with the perimeter of the implant 16 at a shallowest end, and converging to inwardly extending stem 24 in a deepening direction defined by interface 36), as well as opposing lower implant portion 18 (again including post 26) can each further include an undercut textured or otherwise roughened consistency, this contributing to promotion of bone marrow in-growth into the implant portions following such as initial adhesive and seating affixation, such bone growth contributing to long term retention of the implant.

Figure 4:
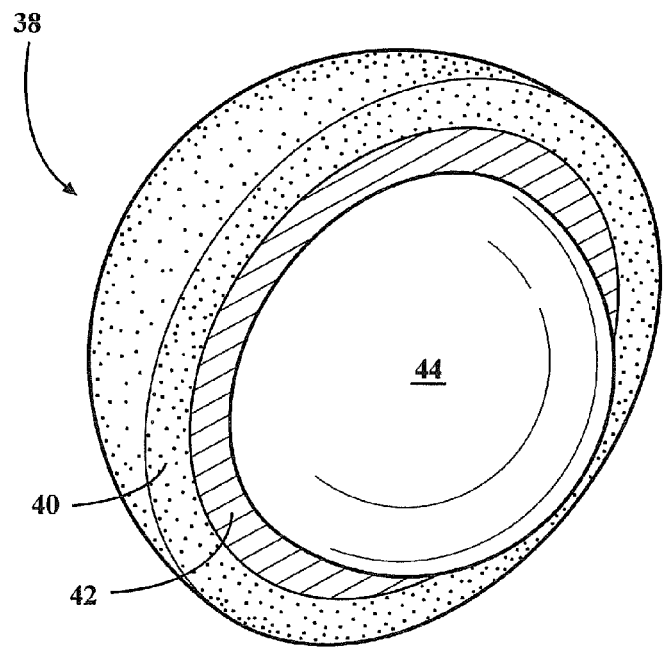
FIG. 4 is a pseudo cutaway view of a spherical shaped intermediate support and which illustrates its multi-material construction with softer outermost shell material and intermediate harder material in cutaway, combined with innermost harder core material in spherical perspective and which further evidences an eccentric rotatable interface established between said intermediate and innermost layers.

Referring now to FIG. 4, a cutaway view is generally shown at 38 of a selected spherical inter-movable support, such as again represented by the spherical ball disclosed in the preceding described variant of FIG. 1. The pseudo cutaway view of FIG. 4 illustrates one non-limiting example of a multi-layer material construction and which includes a softer (typically plastic or plastic composite) outermost material layer 40, an intermediate harder 42 material (typically another plastic), and an innermost harder material 44 (which is depicted in un-sectioned spherical perspective shape and can be of a similar hardness as the intermediate layer 42 as well as potentially including either of a relatively harder or softer material based on the specifics and preferences of the application).

In operation, an eccentric rotatable interface is established between the intermediate 42 and innermost (or core) 44 layers, this typically arising from the compressive aspects exerted on the softest outer shell layer 40 by both the upper and lower associated implants resulting in a degree of inter-rotative offset or eccentric give or play established at the interior interface boundary between the intermediate layer 42 and the inner core 44. The outer compressive exerted forces typically result from any inwardly angular directed force exerted on the intermediate spherical element, and such as is defined as a non-tangential force.

Figure 5:
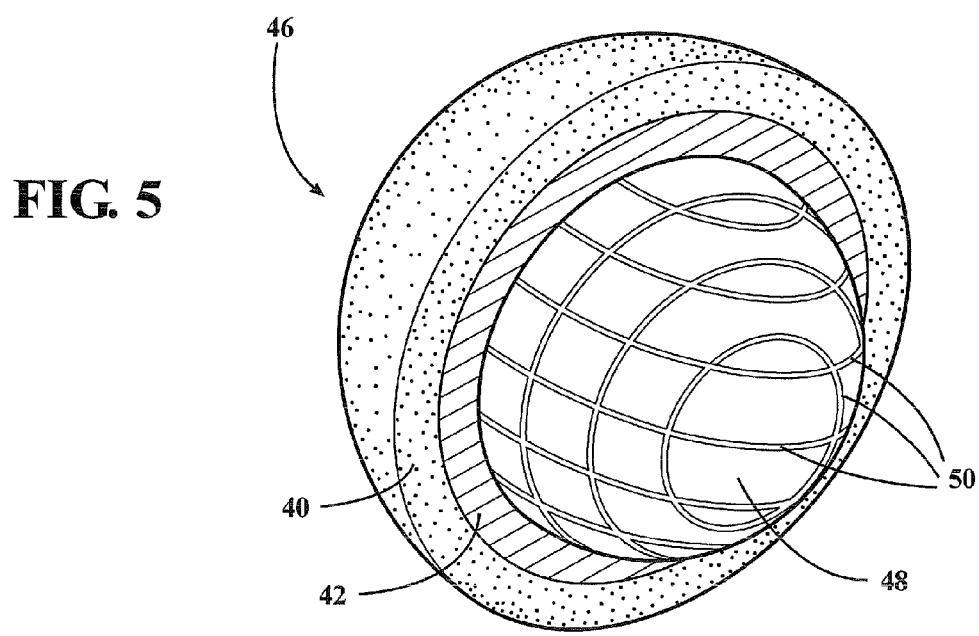
FIG. 5 is a pseudo cutaway view of a spherical shaped intermediate support similar to that in FIG. 4 and further depicting a plurality of lubricant supporting grooves defined in a surface grid pattern associated with the innermost hardened core.

FIG. 5 is a similar pseudo cutaway view, generally at 46, of a spherical shaped intermediate support similar to that in FIG. 5, with identical outer soft shell 40 and intermediate harder shell 42, and in which an innermost core is reconfigured as shown at 48 with a grooved arrangement 50. The grooves 50 can facilitate eccentric motion in the interior boundary defined between layers 42 and 48, in the manner previously described, and/or can also includes entrainment of a volume of lubricant supported within the grooves 50 in a fairly evenly distributed fashion associated with the hardened core 48.

It is also envisioned and understood that the spherical ball, grooves or other supporting structure can include small entrapment channels or pockets for retaining micro particles of debris, either or both plasticized resulting from wear of the implant portions and bone, and such as is further defined as debris osteolysis. The ability to segregate and remove such micro particles (again using the pattern of grooves 50 or other suitable arrangement) assists in extending useful life of the implant along with reducing pain, squeak/noise or other undesirable aspects typical of previous implant designs.

Figure 6:
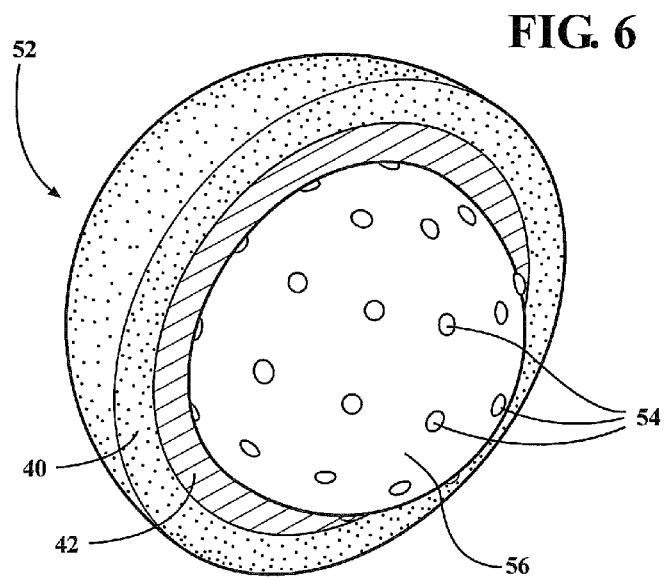
FIG. 6 is a further cutaway view which is again similar to FIG. 4 and further depicting a plurality of substantially surface embedded ball bearings associated with the inner most core.
Figure 7:
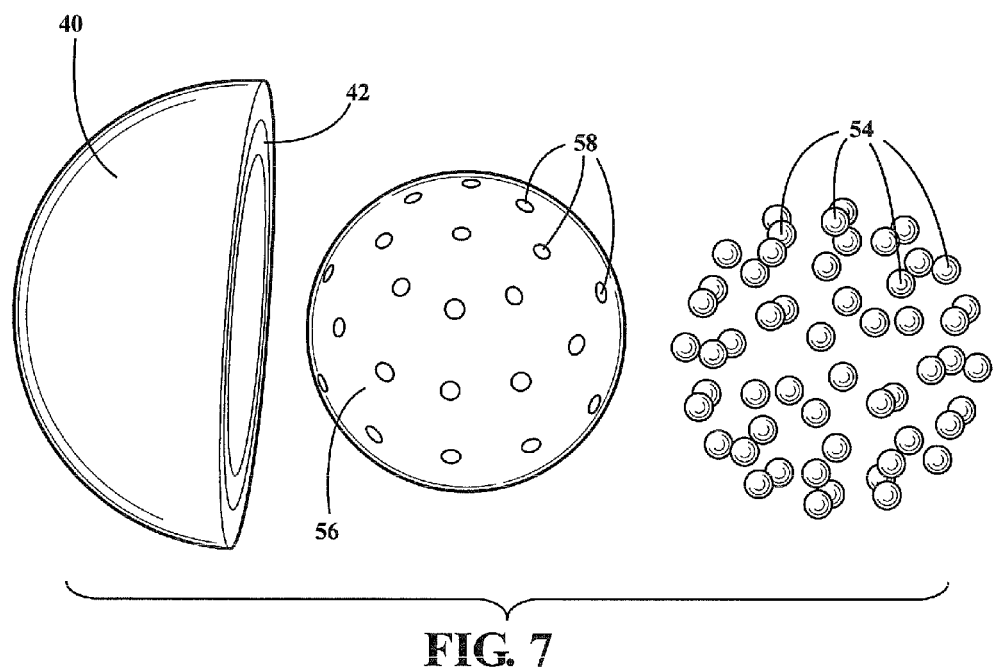
FIG. 7 is an exploded view of the cutaway of FIG. 6 and which better illustrates the arrangement of micro sized ball bearings in combination with the seating locations arranged about the spherical exterior surface of the harder core material.

Referring now to FIG. 6, a further cutaway view is generally shown at 52 which is again similar to FIG. 4 and further depicting a plurality of substantially surface embedded ball bearings 54, such as which can each be constructed of metal, hard plastic or any other suitable material and associated with a further redesigned version of an inner most core 56. As best depicted in the further exploded view of FIG. 7, the ball bearings 54 are separated from the hardened inner spherical core 56, thereby revealing substantially spherical shaped pockets 58 defined across the exterior profile of the core 56 and which substantially seat the individual bearings 54 in a manner which permits the tips thereof (again FIG. 6) to project in a manner which facilitates additional eccentric support motion with respect to the interior interface boundary established with the intermediate later in a manner consistent with the dynamic environments referenced in relation to FIGS. 4 and 6.

Having described my invention, other and additional preferred embodiments will become apparent to those skilled in the art to which it pertains, and without deviating from the scope of the appended claims.

The invention claimed is:

1. A multi-component hallux joint assembly incorporated into reconditioned end surfaces established between an upper metatarsal bone and an opposing lower proximal phalanx bone, said assembly comprising:
   a first component adapted to being anchored into a reconditioned end surface of the metatarsal bone and exhibiting a first exposed support surface;
   a second component adapted to being anchored into a reconditioned end surface of the proximal phalanx and exhibiting a second exposed support surface;
   an intermediate component supported in a rotational fashion between said first and second anchored components, said intermediate component further including a spherical shaped component; and
   said spherical shaped component further including a multi-layer composition including a softer outer layer and at least one harder interior layer, first and second inner layers of said spherical component establishing a rotational interface therebetween.

2. The joint assembly as described in claim 1, each of said anchored components further exhibiting a concave surface for supporting said intermediate component.

3. The joint assembly as described in claim 1, each of said first, second and intermediate components further being constructed of at least one of a metal, plastic, polymer or composite material.

4. The joint assembly as described in claim 1, further comprising a grid pattern of lubricating grooves defined in a surface of an innermost spherical shaped portion of said spherical component facilitating said rotational interface.

5. A multi-component hallux joint assembly incorporated into reconditioned end surfaces established between an upper metatarsal bone and an opposing lower proximal phalanx bone, said assembly comprising:
   a first component adapted to being anchored into a reconditioned end surface of the metatarsal bone and exhibiting a first exposed support surface;
   a second component adapted to being anchored into a reconditioned end surface of the proximal phalanx and exhibiting a second exposed support surface;
   a spherical shaped intermediate component supported in a rotational fashion between said first and second anchored components;
   said spherical shaped component further including a multi-layer composition including a softer outer layer and first and second inner layers establishing a rotational interface therebetween; and
   each of said anchored components further exhibiting a concave surface for supporting said intermediate component.

6. The joint assembly as described in claim 5, each of said first, second and intermediate components further being constructed of at least one of a metal, plastic, polymer or composite material.

7. The joint assembly as described in claim 5, further comprising a grid pattern of lubricating grooves defined in a surface of an innermost spherical shaped portion of said spherical component facilitating said rotational interface.

8. A multi-component hallux joint assembly incorporated into reconditioned end surfaces established between an upper metatarsal bone and an opposing lower proximal phalanx bone, said assembly comprising:

a first component adapted to being anchored into a reconditioned end surface of the metatarsal bone and exhibiting a first exposed support surface;

a second component adapted to being anchored into a reconditioned end surface of the proximal phalanx and exhibiting a second exposed support surface; and an intermediate component supported in a rotational fashion between said first and second anchored components, said spherical shaped component further comprising a multi-layer composition including a softer outer layer and first and second inner layers establishing a rotational interface therebetween.

9. The joint assembly as described in claim 8, each of said anchored components further exhibiting a concave surface for supporting said intermediate component.

10. The joint assembly as described in claim 8, each of said first, second and intermediate components further being constructed of at least one of a metal, plastic, polymer or composite material.

11. The joint assembly as described in claim 8, further comprising a grid pattern of lubricating grooves defined in a surface of an innermost spherical shaped portion of said spherical component facilitating said rotational interface.

\* \* \* \* \*